(12) United States Patent
Caron et al.

(10) Patent No.: US 7,403,673 B2
(45) Date of Patent: Jul. 22, 2008

(54) OPTICAL FIBER POLARIMETRIC CHEMICAL SENSOR

(75) Inventors: Serge Caron, Saint-Augustin-de-Desmaures (CA); Claude Paré, Saint-Augustin-de-Desmaures (CA); Bruno Bourliaguet, Quebec (CA)

(73) Assignee: Institut National d'Optional, Québec (CA)

( * ) Notice: Subject to any disclaimer, the term of this patent is extended or adjusted under 35 U.S.C. 154(b) by 35 days.

(21) Appl. No.: 11/437,034

(22) Filed: May 19, 2006

(65) Prior Publication Data
US 2007/0269174 A1 Nov. 22, 2007

(51) Int. Cl.
*G02B 6/00* (2006.01)
(52) U.S. Cl. .......................... 385/12; 385/123
(58) Field of Classification Search ............ None
See application file for complete search history.

(56) References Cited

U.S. PATENT DOCUMENTS

| | | | |
|---|---|---|---|
| 5,515,459 A * | 5/1996 | Farhadiroushan | 385/12 |
| 5,640,234 A * | 6/1997 | Roth et al. | 356/128 |
| 6,208,776 B1 * | 3/2001 | Prohaska et al. | 385/13 |
| 6,753,520 B2 | 6/2004 | Spirin et al. | |
| 2002/0041723 A1 * | 4/2002 | Ronnekleiv et al. | 385/12 |
| 2002/0131737 A1 * | 9/2002 | Broeng et al. | 385/123 |
| 2003/0174985 A1 * | 9/2003 | Eggleton et al. | 385/125 |

OTHER PUBLICATIONS

Swart et al; Recent Progress in Open Tubular Liquid Chromatography; Trends in Analytical Chemistry; 1997; pp. 332-341; vol. 16, No. 6; Elsevier Science B.V.
Snyovec et al; Chemical Sensing of In-Situ Extracted Organics by Direct Detection of Mode-Filtered Light; Chemical, Biochemical, and Environmental Fiber Sensors VI; Jul. 26-27, 1994; jvol. 2293; SPIE—The International Society for Optical Engineering; San Diego, Ca, USA.
Zhou et al; A Fibre-Optic Mode-Filtered Light Sensor for General and Fast Chemical Assay; Measurement Science and Technology; 2004; pp. 137-142; vol. 15; Institute of Physics Publishing; U.K.
Xi et al; Axial-Beam On-Column Absorption Detection for Open Tubular Capillary Liquid Chromatography; Anal. Chem.; 1990; pp. 1580-1585; vol. 62; American Chemical Society; USA.

(Continued)

*Primary Examiner*—Sung Pak
*Assistant Examiner*—Mike Stahl
(74) *Attorney, Agent, or Firm*—Carter & Schnedler, P.A.

(57) ABSTRACT

The invention relates to distributed optical waveguide polarimetric chemical analysis. Real-time monitoring of a separation process of a fluid in a capillary column is provided using a distributed sensor comprising a birefringent optical waveguide placed between two polarizers. The optical waveguide has a longitudinal channel defined by a channel surface in its cladding and adapted to receive the fluid such that it travels in said longitudinal channel. The longitudinal channel is positioned with respect to the core such that channel surface absorption of the fluid traveling in the longitudinal channel causes a local variation of the orientation of the polarization axes of the optical waveguide. The proposed embodiment can be used for monitoring the velocity of the separated components along the channel.

20 Claims, 7 Drawing Sheets

OTHER PUBLICATIONS

Foster et al; Liquid Chromatographic Sensing in Water on a Thin-Clad Optical Fiber by Mode-Filtered Light Detection; Anal. Chem.; 1996; pp. 1456-1463; vol. 68; American Chemical Society; USA.

Khomenko et al; Wavelength-Scanning Technique for Distributed Fiber-Optic Sensors; Optics Letters; Dec. 1, 1993; pp. 2065-2067; vol. 18, No. 23; Optical Society of America.

Jinno et al; Recent Trends in Open-Tubular Capillary Electrochromatography; Trends in Analytical Chemistry; 2000; pp. 664-675; vol. 19, No. 11; Elsevier Science B.V.

Matejec et al; Improvement of the Sectorial Fiber for Evanescent-Wave Sensing; Sensors and Actuators B; 1997; pp. 334-338; vol. 38-39; Elsevier Science S.A.

* cited by examiner

OPTICAL FIBER POLARIMETRIC CHEMICAL SENSOR

BACKGROUND OF THE INVENTION

1. Field of the Invention

The present invention relates to optical fiber sensors and, more particularly, to distributed optical fiber chemical analysis.

2. Background Art

Simultaneous monitoring of multiple parameters is becoming a growing need in a variety of environments and applications. Distributed and quasi-distributed fiber-optic sensors capable of such functionality are one of the most promising approaches to address these issues and to provide new possibilities in intelligent monitoring systems.

Specialty optical fibers and micro-fabrication techniques make it possible to produce optical fibers with integrated transducer elements. This is especially interesting for chemical sensing with fiber-optic sensors. Chemical sensing represents certainly a potential for fiber-optic sensors, since it is essential in major application domains such as biomedical, food-processing, environment and industrial process monitoring.

In capillary column gas chromatography, a small quantity of a gas mixture is injected at the entrance of a capillary and carried through it by an inert gas flow, called the carrier gas. Along its path the mixture is separated into its components because each of them has a different rate of elution. These rates differ due to differences in the adsorption (gas-solid) or partition (gas-liquid) process that happens at the internal capillary wall. The type of process controlling the separation depends on the chemical composition of the internal capillary surface. For the adsorption process, layers of molecules settle directly on the solid surface as a condensate and for the partition process molecules are dissolved in a thin liquid polymer film. If the separation is effective, pure chemicals are detected one after the other at the exit of the capillary column.

In open tubular liquid chromatography (see Jinno, K. and H. Sawada (2000), "Recent trends in open-tubular capillary electrochromatography", TrAC Trends in Analytical Chemistry 19(11): 664-675 and Swart, R., J. C. Kraak, et al. (1997), "Recent progress in open tubular liquid chromatography", Trends in Analytical Chemistry 16(6): 332) the mobile phase carrying the sample to be analyzed in the column is liquid.

Other types of chromatographies using capillaries exist. Each capillary chromatography uses a reversible interaction of the chemical compounds dissolved in the mobile phase with the capillary surface or a stationary phase covering the capillary surface. The chemical interactions involved in the process comprise adsorption, dissolution, chemisorption, ionic exchange or any other interaction involving the reversible taking of matter by another matter. The term absorption is used herein to designate any of these or other chemical interactions. The term absorption is used to designate chemical absorption as opposed to light or power absorption.

Many chemical sensors based on micro-structured fibers measure the integral of the analyte optical properties (usually absorbance) along the fiber length. Therefore, for a given mixture, these sensors would register the same signal, whether or not the mixture has been separated. A chromatogram can be constructed by measuring the variation of this integral in time as the various separated components exit the capillary (see Xi, X. and E. S. Yeung (1990). "Axial-Beam On-Column Absorption Detection for Open Tubular Capillary Liquid Chromatography." Anal. Chem. 62: 1580-1585). Another approach for real-time monitoring of a separation process is the use of a distributed sensor that allows monitoring of the separation process along the capillary.

One kind of distributed fiber optics sensor is the white-light polarimetric sensor (see Khomenko, A. et al. (1998). "Wavelength-scanning technique for distributed fiber-optic sensors", Op. Lett., 18, pp. 2065-2067.). This kind of sensor makes use of a birefringent optical fiber placed between two linear polarizers. White light is injected at one end and the transmitted spectrum is recorded at the other end. Small local perturbations along the fiber create coupling between the two polarization modes carried by the birefringent fiber and each of these mode coupling events is contributing to the apparition of peaks in the Fourier spectrum of the transmitted signal.

Another option is a Mode-Filtered Light Detection system as provided in Zhou, L., K. Wang, et al. (2004); Synovec, R. E., C. A. Bruckner, et al. (1994); Foster, M. D. and R. E. Synovec (1996). A multimode optical fiber is inserted in a chromatography capillary and absorption of the analyte at the surface of the optical fiber results in higher-order modes leakage detected on the side of the optical fiber. In such a configuration, light detection could be very sensitive to light injection conditions and the system is likely to be very unstable. Such a system is also sensitive to fiber bending and it is thus not possible to wind the capillary column as is typically done in chromatography.

SUMMARY OF INVENTION

It is therefore an aim of the present invention to provide a distributed optical fiber polarimetric sensor adapted to perform chemical analysis by chromatography.

Therefore, in accordance with a first aspect of the present invention, there is provided an optical waveguide analyzing system. The system comprising a light source system for providing a polarized source light, a birefringent optical waveguide optically coupled to the light source system such that the light is to be propagated in the optical waveguide, and an analyzing module optically coupled to the optical waveguide. The optical waveguide has a propagation volume extending along the optical waveguide, with at least a portion of the light to be confined thereto, a cladding volume extending along the optical waveguide and surrounding the propagation volume, a first and a second polarization axes, and a longitudinal channel defined by a channel surface in the cladding volume and adapted to receive a fluid such that the fluid travels along the longitudinal channel, the longitudinal channel being positioned with respect to the propagation volume in such a manner that the fluid traveling in the longitudinal channel is to cause a local variation of the orientation of the polarization axes. The analyzing module is for polarizing an outgoing light and for providing a measurement of an effect of the local variation of orientation on the polarized outgoing light so as to analyze at least one characteristic of the fluid.

In accordance with a second aspect of the present invention, there is provided an optical waveguide wherein a fluid is to travel and wherein light is to be propagated. The optical waveguide comprising a propagation volume extending along the optical waveguide, with at least a portion of the light to be confined thereto; a cladding volume extending along the optical waveguide and surrounding the propagation volume; a first polarization axis associated with a first effective index and a second polarization axis associated with a second effective index, a value of the first effective index and a value of the second effective index being different in such manner that the optical waveguide is a birefringent waveguide; and a longitudinal channel defined by a channel surface in said cladding volume and wherein the fluid is to travel, the channel being positioned with respect to the propagation volume in such a manner that the fluid traveling in the channel is to cause a local variation of the orientation of the polarization axes.

BRIEF DESCRIPTION OF THE DRAWINGS

Having thus generally described the nature of the invention, reference will now be made to the accompanying drawings, showing by way of illustration a preferred embodiment thereof and in which.

DESCRIPTION OF THE PREFERRED EMBODIMENTS

Figure 1A:
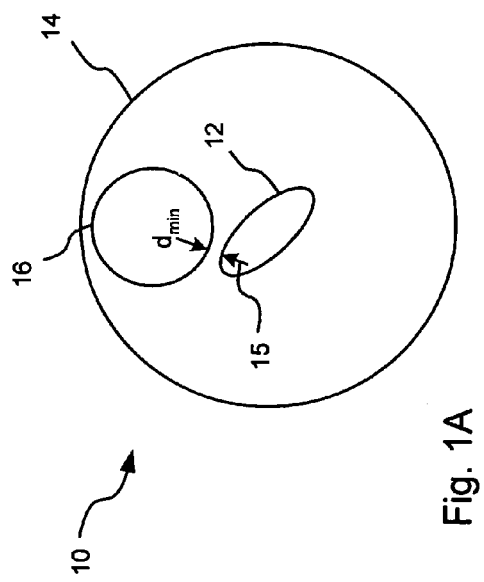
FIG. 1A is a cross sectional view of a modified birefringent optical fiber according to one embodiment of the present invention, wherein the optical fiber has a core with a non-circular symmetry and an uncoated channel wherein a fluid is to be circulated.

Real-time monitoring of a separation process can be done by using a distributed sensor, which measures interactions of the analyte components with a capillary column as it travels therein. With such a sensor, both positions and velocities of the interactions are monitored. However, it should be appreciated that components separate as each one flows at its own velocity in the capillary. Accordingly, a separation process may be characterized by monitoring the distributed velocities of the selected separated components in the capillary. The proposed embodiment can be used for monitoring either the distributed velocities or both the distributed velocities and the distributed positions of the separated components.

In a birefringent optical fiber, linearly polarized light will travel at different speeds, depending along which polarization axis its polarization is aligned. These axes are referred to as the slow and fast axes. If unperturbed, both polarization axes can then be considered as two independent channels of unequal lengths. Arranged in a proper configuration, a birefringent fiber can act as a two-beam interferometer.

As an example, when linearly polarized light from a white light source is injected into the fiber at 45° with respect to the polarization axes, both polarization eigenmodes are excited. With an analyzer oriented also at 45° at the end of the fiber, an optical spectrum analyzer will record an interferogram described by the following relation:

$$I = I_0 \left[ \frac{1}{2} + \frac{1}{2} \cos\left(\frac{2\pi}{\lambda} \Delta n L\right) \right], \quad (1)$$

where $\Delta n$ is the effective refractive index difference between the two axes, L represents the fiber length, $\Delta nL$ thus corresponds to the path difference between the eigenmodes. $I_0$ describes the wavelength-dependent input intensity.

By introducing perturbations at discrete points along the birefringent optical fiber, the polarimetric interferometer response will change as a result of the coupling between the polarization eigenmodes. Considering the case where the input light is polarized along one of the polarization axes and where the analyzer is oriented at 45°, the transmitted intensity can be expressed in the following form, if the coupling coefficient is weak ($\kappa \ll 1$):

$$I = I_0 \left[ \frac{1}{2} - \sqrt{\kappa} \cos(2\pi \nu \Delta n L) \right], \quad (2)$$

where $\nu = 1/\lambda$ is the wavenumber and $\kappa$ is the coupling coefficient.

If an optical fiber polarimetric interferometer is configured in such a way that the perturbations are introduced by a phenomenon in the fiber core environment, whether it is chemical, physical or biological, then the interferometer acts as a sensor. If many mode coupling points are used to achieve distributed sensing, the interferometer response, in the approximation of weak coupling coefficients, becomes:

$$I = I_0 \left[ \frac{1}{2} - \sum_{n=1}^{N} \sqrt{\kappa_n} \cos(2\pi \nu \Delta n Z_n) \right] \quad (3)$$

where N represents the number of mode coupling points and $Z_n$ is their distance from the fiber end. The Fourier transform of this interferogram yields an intensity profile spectrum as a function of the position z on the optical fiber, corresponding to a signature of the coupling perturbations along the optical fiber, and their relative strength $\kappa_n$ can be inferred from it. Under appropriate conditions, the relative strengths $\kappa_n$ can be used in chemical analysis of a fluid when it is related to the amount of fluid absorbed in the mode coupling region. Quantitative analysis can thus be provided.

FIG. 1A depicts a schematic view of a modified birefringent fiber 10 that is appropriate for an application in fluid analysis. The birefringent optical fiber 10 is modified to introduce a fluid that can induce mode coupling between the two polarization modes of the optical fiber 10. A large longitudinal channel 16 in the fiber cladding 14 and located near the fiber core 12 allows introduction of the fluid. The optical fiber 10 consists of a birefringent fiber having a non-circular core, elliptical for instance, and a channel 16 both mostly defining the orientation of the two polarization axes of the fiber. A local presence of a fluid travelling at the surface of the channel affects the local orientation of the polarization axes as the fluid flows in the channel 16. Local absorption concentrates the fluid components at the surface of the channel producing more efficient local perturbations of the polarization axes and providing more effective polarization mode coupling.

The channel 16 is close to the core 12 and, in this embodiment, its centre is along a line at approximately 45° relative to the major and minor axes of the core so that a local presence of a fluid circulating at the surface of the channel 16 will operatively affect the local orientation of the polarization axes causing polarization mode coupling. The channel 16 could otherwise be positioned given that it disturbs the symmetry of the cross-section of the optical fiber 10. For example, the angle between the line and the major an minor axes of the core could be varied. In the optical fiber 10, the cladding 14 mostly confines light in the core 12 which acts as a propagation area, while light also propagates in part in the cladding 14 and in the channel 16.

Figure 1B:
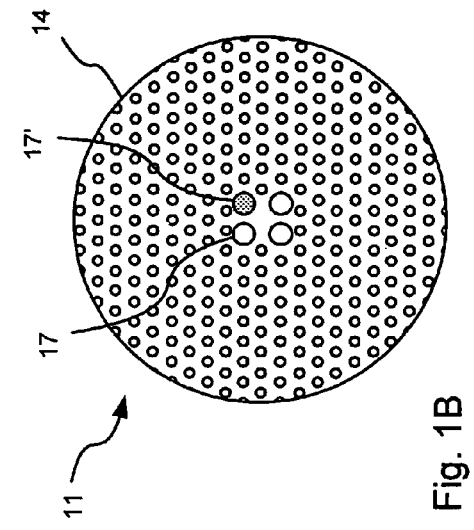
FIG. 1B is a cross sectional view of a birefringent microstructured optical fiber according to another embodiment of the invention, wherein a fluid is flowing in one of the holes of the microstructured optical fiber which provides the channel.
Figure 1C:
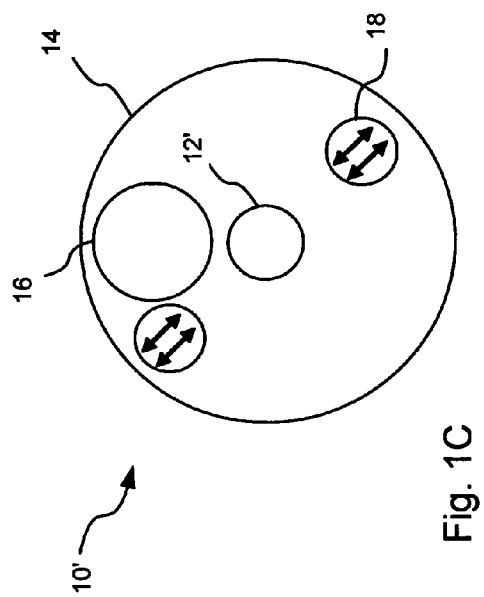
FIG. 1C is a cross sectional view of a modified birefringent optical fiber according to another embodiment of the present invention, wherein the optical fiber has a circular core and stress-inducing features.
Figure 1D:
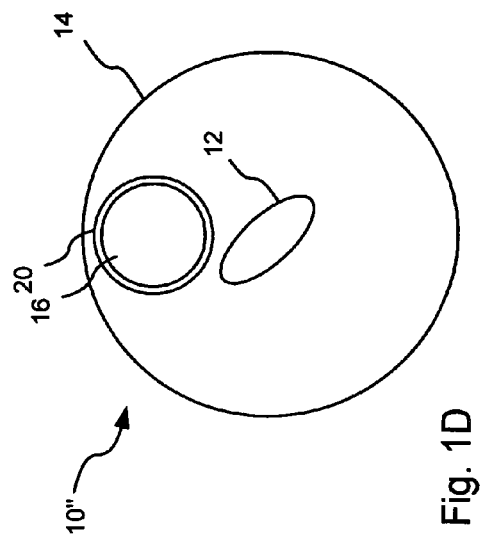
FIG. 1D is a cross sectional view of a modified birefringent optical fiber, wherein the optical fiber has a non-circular core and a channel having a surface treatment used as a stationary phase in the absorption process.

One skilled in the art will understand that the proportions of the features of the fiber 10 as shown in FIG. 1A, as well as the proportions in FIG. 1B, FIG. 1C and FIG. 1D, has been exaggerated for better illustration and that the size of the core 12 is typically of a few micrometers while the size of the channel 16 is of hundreds of micrometers.

As will be discussed later on, the local rotation angle $\phi$ of the polarization axes depends on the proximity of the channel 16 (the channel 16 needs to be close to the core 12 so that an evanescent wave of the propagated light partly propagates in the channel 16), on the refractive index of the medium that fills it and on the refractive index of the core 12 and the cladding 14. In this embodiment, for ease of fluid introduction and displacement, a relatively large 100 μm diameter was chosen for the channel 16. One possible dimension of the core is a semi-major length of 4.9 μm and a semi-minor length of 1.7 μm. As will be discussed further below, one important design parameter is the minimum distance 15 ($d_{min}$) between the core 12 and the channel 16. One suitable distance 15, $d_{min}$, is 1.6 μm. Those dimensions are given here for illustration, but other dimensions are considered. For example, an alternative suitable value of $d_{min}$ is 0 μm.

FIG. 1B shows an alternative birefringent optical fiber 11 using a microstructured fibre. The shape birefringence is created by the four large holes 17 ensuring birefringence. At least one of these holes, identified as 17', is used to create the channel where a fluid is to be circulated. As in the optical fiber 10 of FIG. 1A, a local rotation of the polarization axes is induced by local absorption or any kind of presence of the fluid.

In the microstructured fiber 11, light is mostly confined in a propagation area produced by the introduction of microstructures in the cladding 14, while light also propagates in part in the cladding 14 and in the holes 17. One should appreciate that other possible microstructured fiber designs could be appropriate as long as the optical fiber is birefringent and as there is one or more channels 16 for receiving the fluid to be analyzed and inducing a local reorientation of the polarization axes.

FIG. 1C shows another embodiment of a birefringent fiber 10'. In this embodiment, the optical fiber has a circular core 12' and birefringence is obtained using stress-inducing features 18.

FIG. 1D shows another embodiment of a birefringent optical fiber 10" similar to the optical fiber 10 of FIG. 1A but comprising a surface treatment 20 on the channel surface to enhance fluid component absorption at the channel surface. The surface treatment 20 is used as a sorbent or stationary phase. One should appreciate that sorption heat or fluid induced stress in the coating participates to mode coupling in the sensor.

In the hereinafter described embodiments, the fluid to be circulated in the optical fiber is typically an homogenous mixture comprising a fluid carrier and one or more components diluted in the fluid carrier. The fluid carrier can be a liquid (liquid carrier) or a gas (gas carrier). It can also be a heterogeneous mixture, as a droplet pushed by a gas along the channel. The fluid includes all the chemical substances flowing in the channel. However, only the chemical substances that are locally absorbed or locally present at the capillary surface, such that they interact with light propagating in the optical fiber, can be detected as those chemical substances participate in the separation of the fluid and in the production of coupling points.

Figure 2B:
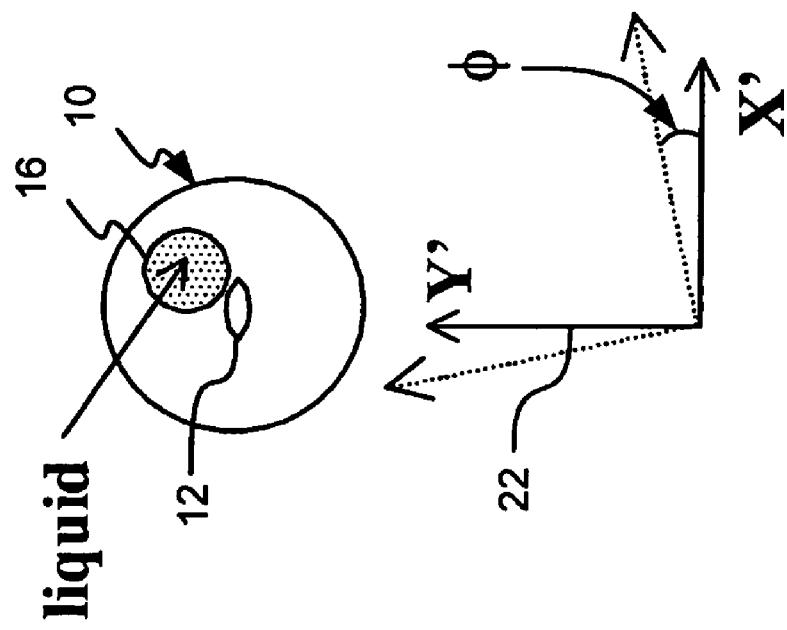
FIG. 2A and FIG. 2B are a schematic illustration of the coupling mechanism, wherein, in FIG. 2A, there is no fluid in the channel and wherein, in FIG. 2B, a fluid flows in the channel.
Figure 2A:
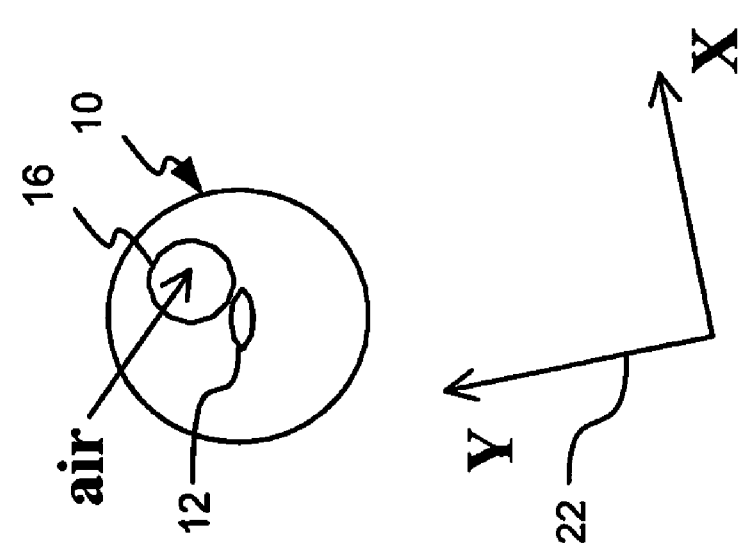

FIG. 2A and FIG. 2B illustrate the polarization coupling mechanism used in a chemical analysis system having the fiber 10. All along the optical fiber 10, the large channel 16 is located close to the elliptical core 12. At some coupling points, the presence of a liquid in the channel 16 induces a local rotation $\phi$ of the polarization axes 22. Similarly, local absorption at the channel surface of a fluid traveling in the channel 16 produces a local rotation $\phi$ of the polarization axes 22. Whether or not this perturbation can be detected depends on the sensor sensitivity which depends on its turn on the fiber design and the amount of absorbed material.

Figure 3:
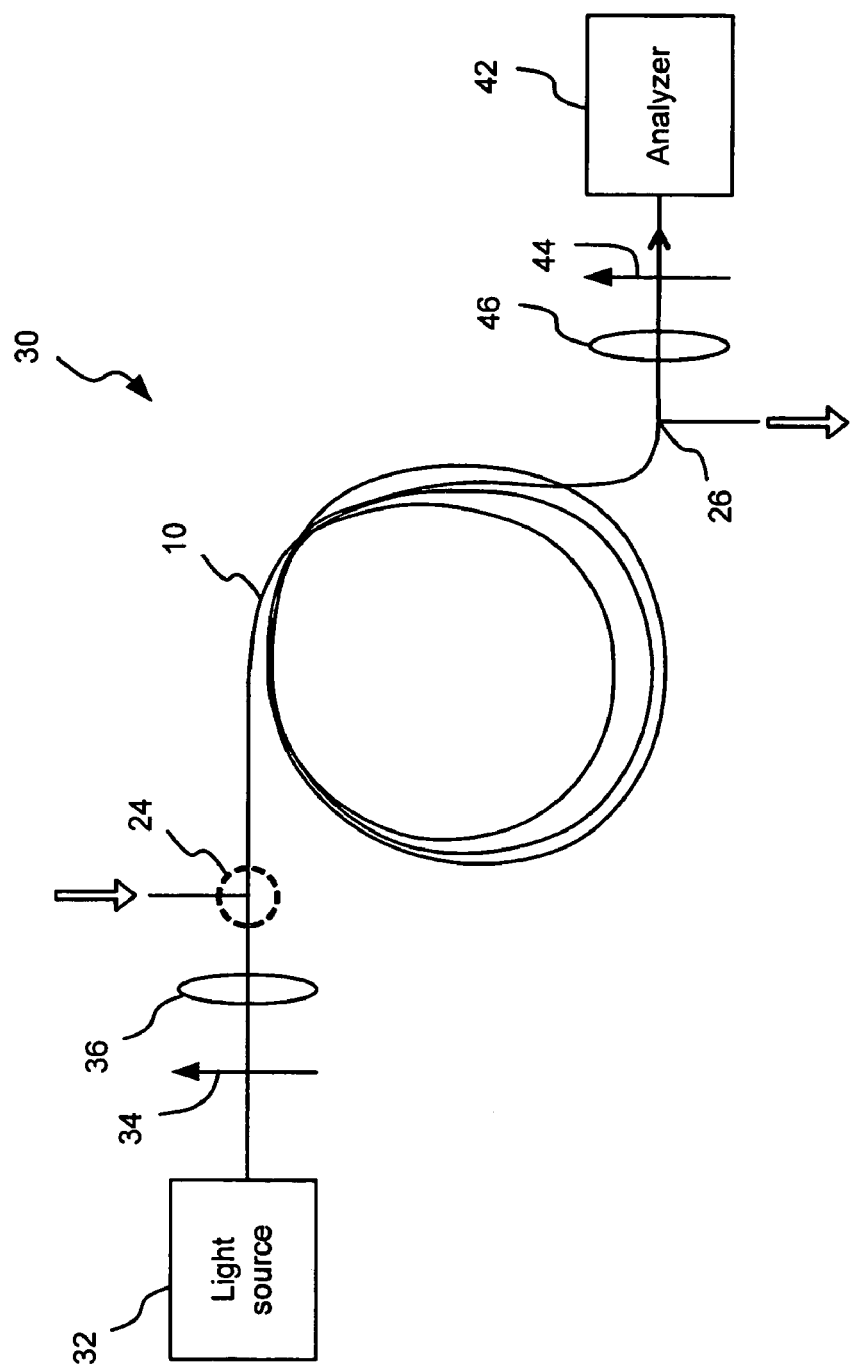
FIG. 3 is a schematic view of a distributed optical fiber chemical analyzing system using the modified birefringent optical fiber of FIG. 1A, wherein light is injected and collected at opposite ends of the optical fiber.

FIG. 3 shows a distributed optical fiber chemical analyzing system 30 using the modified birefringent optical fiber 10 of FIG. 1A. It is pointed out that, although the chemical analyzing system 30 is illustrated with the fiber 10, the fibers 10' (FIG. 1C), 10" (FIG. 1D) and 11 (FIG. 1B) can alternatively be used with the analyzing system 30. A light source system comprises a light source 32, an Amplified Stimulated Emission (ASE) source for instance, a source polarizer 34 to linearly polarize light, and injection optics 36 that injects light at one end of the optical fiber 10.

The source polarizer 34 is oriented so that it provides a polarization direction defining a nearly zero-degree angle with one of the polarization axes of the fiber. Light thus propagates in the optical fiber 10 in mostly one polarization mode.

At the other end of the optical fiber 10, the output light is analyzed using an analyzing system comprising receiving optics 46, a second linear polarizer, the analyzer polarizer 44, and an optical analyzer 42, an optical spectrum analyzer for instance. In this embodiment, the analyzer polarizer 44 defines a 45-degree angle with the source polarizer. Other alignment angles are possible but they would reduce the intensity of the signal modulation. To circulate a fluid into the channel 16 (see FIG. 1A), an inlet transversal conduit 24 is positioned at one end of the fiber 10 and is in fluid communication with the channel 16. An outlet conduit 26 is provided at the other end of the fiber 10 and is in fluid communication with the channel 16 as well. The fluid is circulated in the optical fiber 10 by inducing a pressure difference between the inlet conduit 24 and the outlet conduit 26.

As previously stated, in order to provide a weak coupling condition, the polarization of the input light is nearly aligned with one of the polarization axes of the optical fiber. Actually, the input polarization is preferably slightly skewed in order that a peak corresponding to the fiber length appears on the Fourier spectrum. This peak can be used to normalize the position of the relevant peaks.

In the embodiment of FIG. 3, a broadband Amplified Stimulated Emission (ASE) light source and an optical spectrum analyzer are used but one should appreciate that a tunable broadband light source and an optical detector could be used instead. A broadband analysis provides position information of the separation process in the capillary.

Alternatively, a separation process may be characterized by monitoring only the velocity of the separated components in the capillary using single wavelength analysis. In this case, a single wavelength light source and an optical detector can be used. As one or more coupling points propagates along the optical fiber, the Fourier transform of the time varying signal captured over a given time interval will show a peak corresponding to the velocity of a coupling point. In a separation process of a fluid mixture, different components will propagate at different velocities due to the different elution rates, and the Fourier transform will show multiple peaks.

The inlet conduit 24 and outlet conduit 26 are created by machining the optical fiber 10 through its outer surface such as to access the channel 16. For example, laser drilling can be used for this purpose. The channel 16 is closed off at both extremities of the optical fiber 10. For instance, electrical arc fusion can be used to close off the channel 16 at the extremity of the fiber 10. Alternatively, the cladding holes can be closed off by polymer injection or using adhesives.

Figure 4:
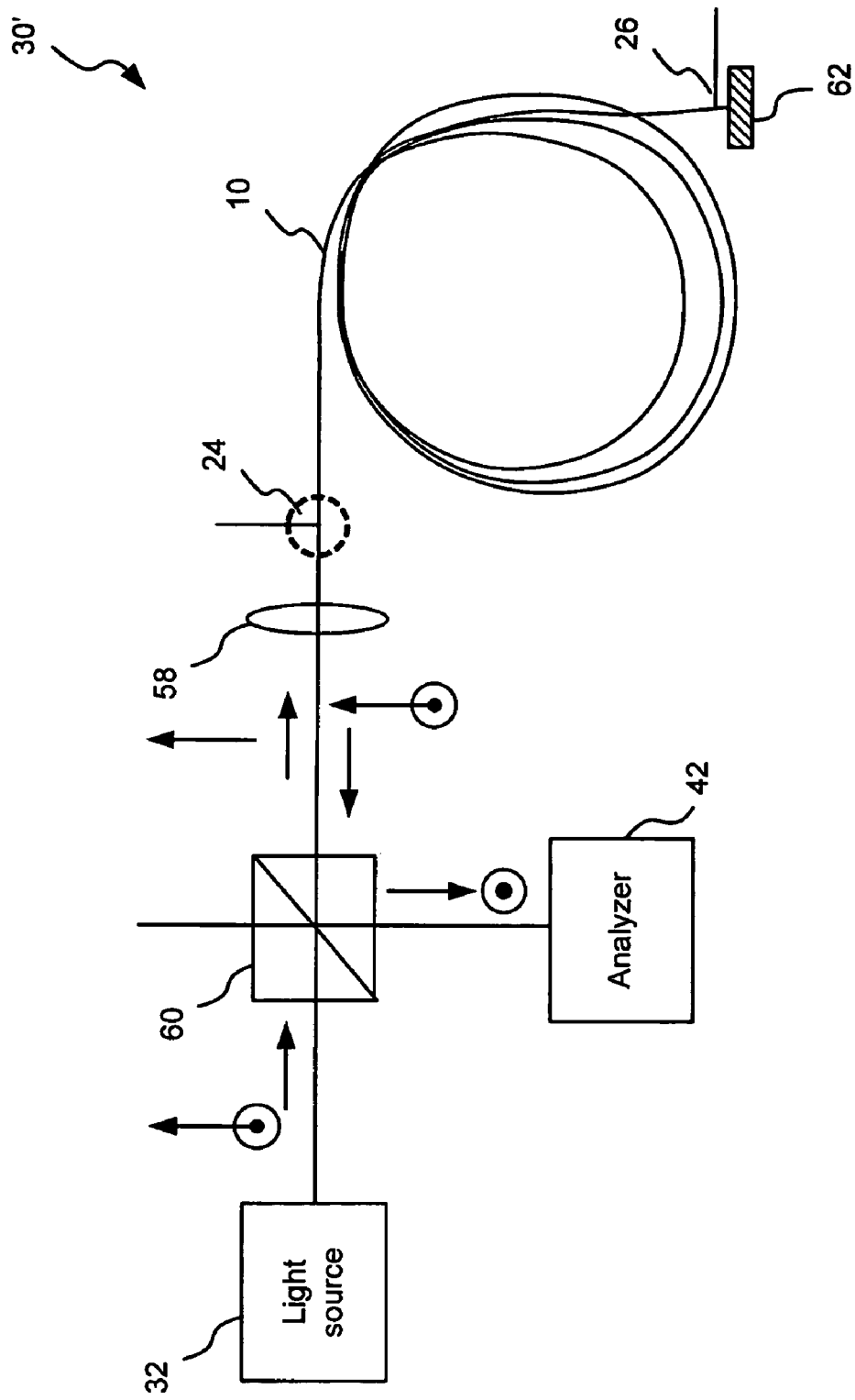
FIG. 4 is a schematic view of a distributed optical fiber chemical analyzing system using the modified birefringent optical fiber of FIG. 1A, wherein light is injected and collected at the same end of the optical fiber.

FIG. 4 illustrates another distributed optical fiber chemical analyzing system 30' in which light is injected and collected at the same input-output end of the optical fiber 10. It is pointed out that, although the chemical analyzing system 30' is illustrated with the fiber 10, the fibers 10' (FIG. 1C), 10" (FIG. 1D) and 11 (FIG. 1B) can alternatively be used with the system 30'. There are similarities between the distributed chemical analyzing systems 30 and 30', whereby like numerals will represent like elements.

In this embodiment, a light source system comprises a light source 32, a polarization beam splitter 60 and injection/reception optics 58. The polarization beam splitter 60 polarizes the input light which is injected in the optical fiber 10 from its first end using the injection/reception optics 58. A reflective device 62, such as a mirror, a gold-coated cleaved fiber face or a fiber Bragg grating, reflects light at the second end of the optical fiber 10. As will be discussed later on, in the case of gold-coated cleaved face and Fiber Bragg gratings, the outlet conduit 26 can alternatively be omitted since the channel opens unto the cleaved end.

Light exiting through the first end of the optical fiber 10 is analyzed using an analyzing system comprising injection/reception optics 58, the polarization beam splitter 60 and an optical analyzer 42. In this embodiment, the polarization beam splitter 60 acts as a polarizing device like the analyzer polarizer 44 of the chemical analyzing system 30 illustrated in FIG. 3.

It should be appreciated that the mirror 62 of FIG. 4 could be directly coated on the optical fiber end, using vapor deposition for example, while keeping the channel opened. The outlet 26 could then be omitted and this coated end of the optical fiber 10 be directly inserted in the injector of a chromatograph as, for instance, the injector model 1041 of a Varian chromatograph. The fluid is then injected at the mirror 62 and the inlet 24 is replaced by an outlet from which the fluid exits the fiber. Alternatively, the mirror could be replaced by a Fiber Bragg Grating and fluid injected similarly.

Alternatively, the systems of FIG. 3 and FIG. 4 could be all-fiber systems if the optical components were fiber pigtailed components. For example, a fiber optics polarization splitter, a 968P from Canadian Instrumentation & Research Ltd., or a polarization maintaining fiber optic coupler could be used as a beam splitter instead of the polarization beam splitter 60 of FIG. 4. In the latter case, fiber optic polarizers are added, as polarization maintaining fiber optic couplers do not polarize light.

Figure 5:
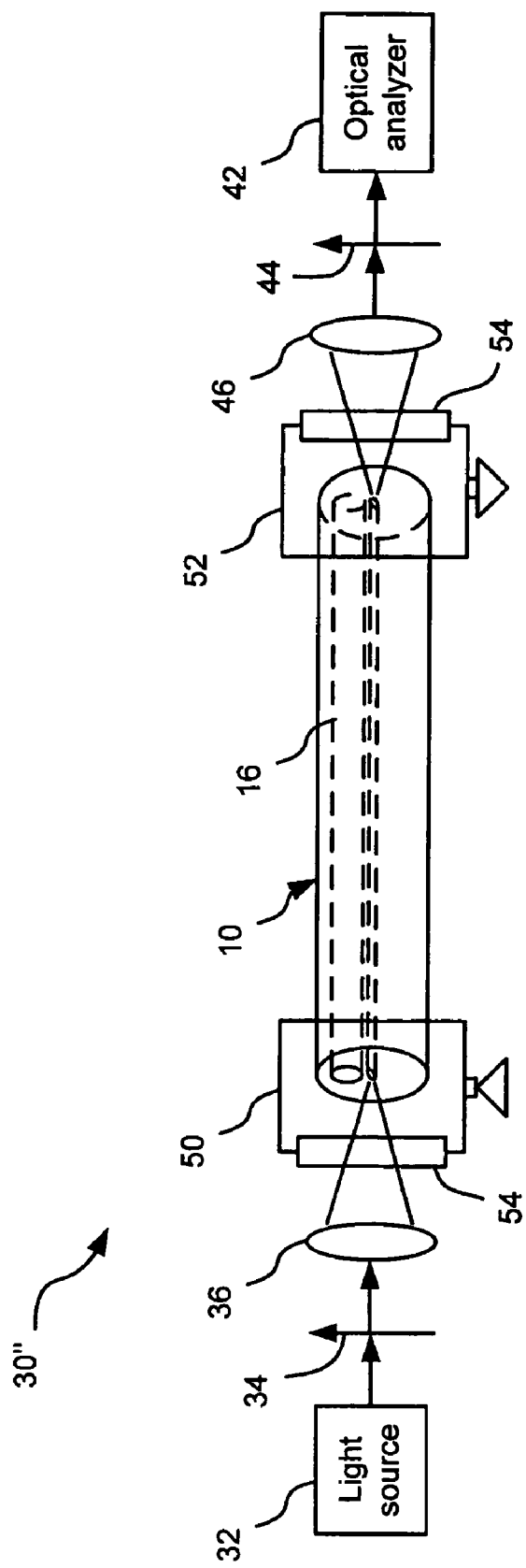
FIG. 5 is a schematic view of a distributed optical fiber chemical analyzing system using the modified birefringent optical fiber of FIG. 1A, wherein light is injected and collected from cleaved end of the optical fiber.

FIG. 5 illustrates yet another distributed optical fiber chemical analyzing system 30" using the optical fiber 10 described above. It is pointed out that, although the chemical analyzing system 30" is illustrated with the fiber 10, the fibers 10' (FIG. 1C), 10" (FIG. 1D) and 11 (FIG. 1B) can alternatively be used with the system 30". In this embodiment, one end of the optical fiber 10 is inserted into an inlet tank 50 and the other end, in an outlet tank 52. Both tanks 50 and 52 are supplied with the fluid to be analyzed. The fluid is circulated by providing a pressure difference between the inlet tank 50 and the outlet tank 52. Each tank 50, 52 has a window 54 facing the cleaved surface of the optical fiber inserted in the tank.

A light source system comprises a light source 32, a source polarizer 34 and injection optics 36 to inject a polarized light into the optical fiber 10. Light reaches the optical fiber through the window 54 of the inlet tank 50. Light exiting the optical fiber 10 from the other end passes through the window 54 of the outlet tank 52 before being collected and characterized using the analyzing system including receiving optics 46, an analyzer polarizer 44 and an optical analyzer 42.

It is contemplated to alternatively use this system in reflection, as for the system of FIG. 4.

Numerical analyses of the sensitivity of the chemical analyzing systems will now be presented. These numerical analyses were carried out using the optical fiber 10 but are generally representative of the behavior of a distributed optical fiber chemical analyzing system according to the present invention.

Figure 6:
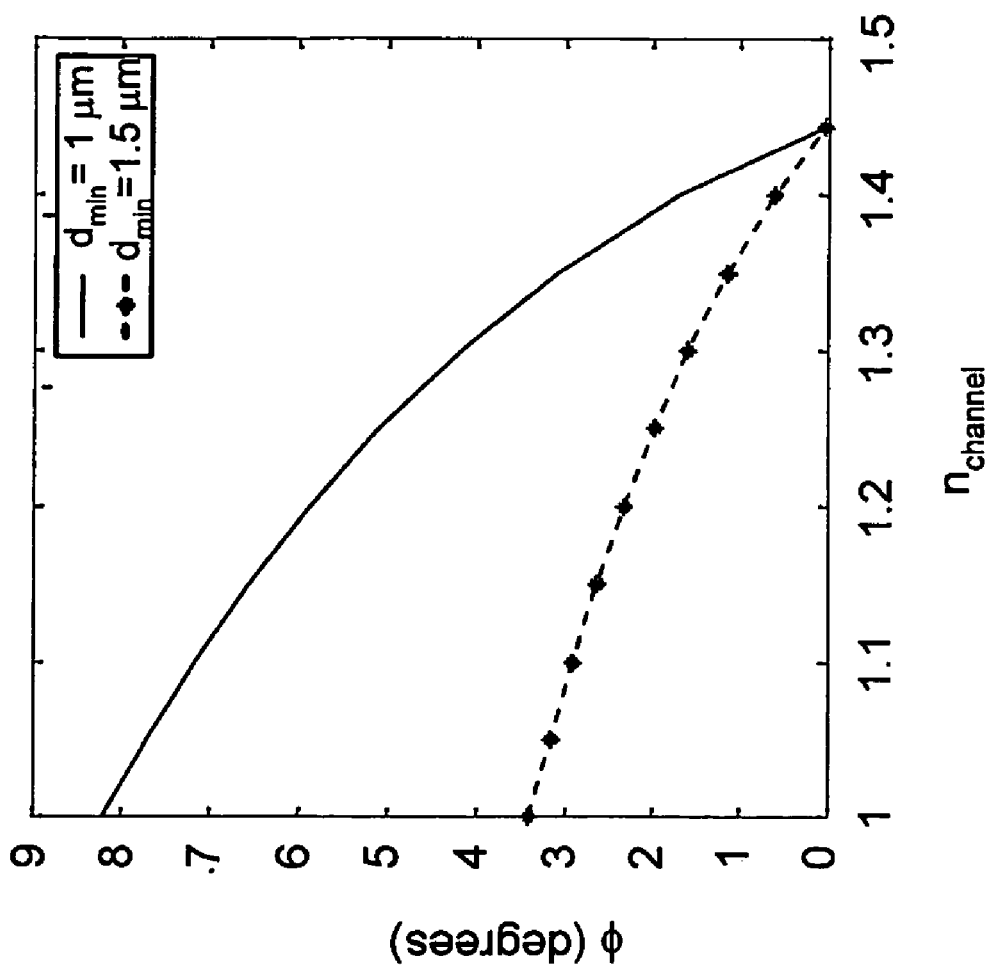
FIG. 6 is a graph showing a relation between a rotation of the polarization axes and a refractive index of a fluid filling the channel, wherein, in the upper curve, the distance $d_{min}$ between the core, having a refractive index of 1.454, and the channel is 1 µm and wherein, in the lower curve, the distance between the core and the channel is 1.5 µm.

Numerical simulations were carried out for a quantitative assessment of the sensitivity of the chemical analyzing system. FIG. 6 shows the influence of the refractive index of the liquid filling the channel on the rotation angle of the polarization axes, $\phi$. The solid and dashed lines correspond to a core-channel minimum separation ($d_{min}$) of 1.0 and 1.5 µm respectively. The shape birefringence of the unperturbed fiber is about $2.2 \times 10^{-4}$ and the refractive index of the core material is 1.454 at the operating wavelength of 1550 nm. The stress-induced birefringence is not considered here.

A finite-difference frequency domain fully vectorial mode solver was used to calculate the two polarization modes at the operating wavelength $\lambda$=1550 nm. To investigate the influence of $d_{min}$ on the rotation angle $\phi$, the case of water (refractive index of 1.333) is considered with the assumption that the entire cross-section of the channel is filled. The results are shown in FIG. 7A.

Figure 7B:
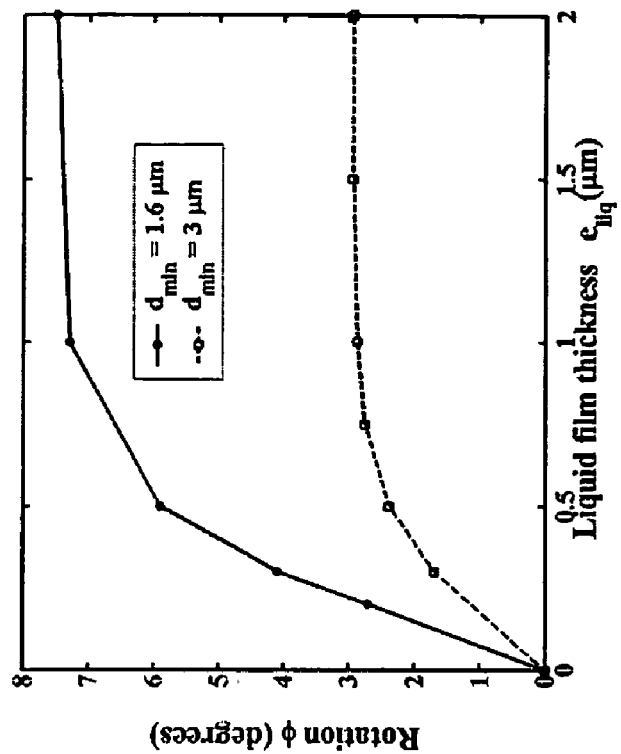
FIG. 7B is a graph showing a relation between a rotation of the polarization axes and a liquid water film thickness on the surface of the capillary.
Figure 7A:
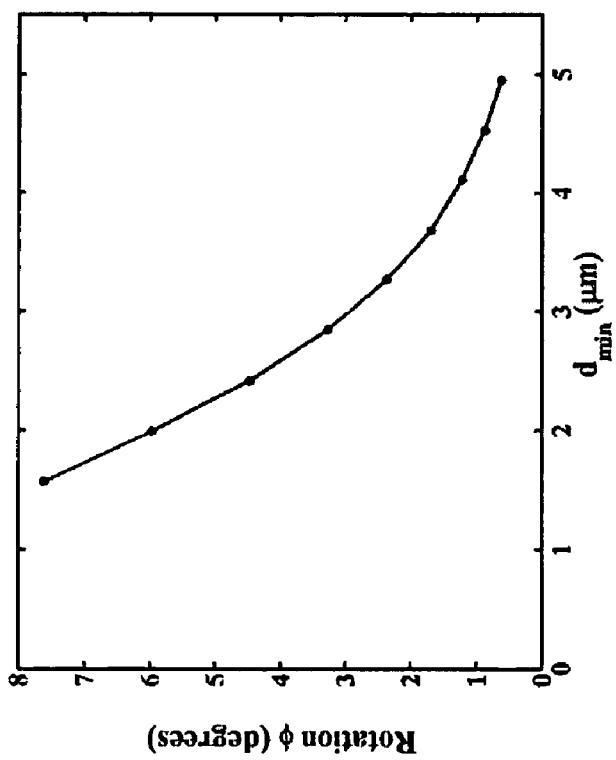
FIG. 7A is a graph showing a relation between a rotation of the polarization axes and the distance between the core and the channel, wherein the channel is filled with water (refractive index=1.333)

FIG. 7A shows the relation between the local rotation $\phi$ of the polarization axes and the distance $d_{min}$ between the core and the channel. The local rotation $\phi$ is found by first calculating the orientation of the polarization axes in absence of fluid. Partial (finite absorbed liquid thickness film $e_{liq}$) or complete filling of the hole by a liquid of refractive index closer to fused silica index tends to reorient the polarization axes, thus inducing the local rotation $\phi$.

It is noticed that, in this specific embodiment, this influence becomes negligible when $d_{min}$ exceeds approximately 6 µm.

In a case where the optical fiber is a micro-structured fiber, as the one depicted at 11 in FIG. 1B, $d_{min}$ is undefined since there is no finite core defined in the micro-structured fiber. The sensitivity thus depends on the overlap of an optical propagation mode and the channel or on the distance between the channel center and the mode center. A channel closer to the mode center will interact more efficiently with the optical propagation mode.

In view of possible applications in chromatographic sensing, the possibilities offered by the fiber 10 depicted in FIG. 1A in the case of a finite liquid film thickness resulting from chemical adsorption on the inner surface of the hole are considered. FIG. 7B shows the relation between the local rotation φ of the polarization axes and a liquid film thickness $e_{liq}$. According to simulations carried out in view of one embodiment, a film thickness of several hundreds of nanometer is required for effective mode coupling. Such a thickness represents hundreds of monolayers and necessitates a surface treatment 20 of the channel 16 as provided in optical fiber 10'' depicted in FIG. 1D to favor large absorption of fluid components. In chemical analysis, the useful regions of the graph of FIG. 7B are the regions where the local rotation φ of the polarization axes is linearly proportional to the liquid film thickness $e_{liq}$, as the local rotation φ is then representative of the taking of matter at the channel surface.

It is pointed out that, in order to simplify the presented numerical simulations, the refractive index of the liquid film is assumed lower than the one of the optical fiber core. However, given that the liquid film is thin, i.e. hundreds of nanometers, light is guided in the optical fiber no matter the refractive index of the liquid film, and the general behavior of the sensor is the same. Further more, a surface treatment of the channel as provided in optical fiber 10'' (see FIG. 1D) does not compromise light guiding, no matter the refractive index of the surface treatment, given that it is sufficiently thin.

As illustrated in the numerical simulations of FIG. 6, the refractive index of a fluid carrier filling the cross-section of the channel should however be lower than the one of the optical fiber core in order to prevent light to be guided in the channel while it should be guided in the core.

Theoretical analysis and modeling of the behavior and limitations of the distributed optical fiber chemical. analyzing system will now be discussed in detail.

Polarization Interferometry

First, measurement of the position z of a coupling point is discussed. Along a birefringent fiber, a phase delay develops between the two polarization modes Ex and Ey. Assuming that at some point along the fiber, a coupling mechanism ensures the presence of both modes, the passage of the outgoing signal through an analyzer, consisting of a polarizer inclined at 45°, gives rise to a beating in the spectral domain (ν=1/λ):

$$I(v) = \frac{I_x}{2} + \frac{I_y}{2} + \sqrt{I_x I_y} \cos(2\pi B v z), \tag{4}$$

where z represents the distance from the coupling point to the analyzer, B is the fiber birefringence and $I_{x,y}=|E_{x,y}|^2$. Normalization of the output signal to the source spectrum eliminates the source spectral dependency and singles out the frequency beatings. The Fourier transform (as a function of the distance variable z) of the normalized spectrum then gives rise to a peak whose position is directly related to the beating frequency $1/(B\,z)$. From the measured birefringence B, the position z of the coupling point is calculable.

Coupling Points

It is firstly assumed that the injected signal excites only one of the two polarization modes E0y which is maintained up to a first coupling point where both local polarization modes Ex' and Ey' are then excited and propagate over a short perturbed birefringent section of length 1'; at the exit of that zone, the resulting elliptically polarized signal will then excite both polarization modes Ex et Ey of the unperturbed birefringent fiber. Assuming that the perturbation only changes the local orientation of the polarization modes (a similar assumption is generally done for the treatment of polarization mode dispersion, for example), the passage through the coupling zone can be described in terms of Jones matrices:

$$\begin{pmatrix} E_x'' \\ E_y'' \end{pmatrix} = \begin{pmatrix} \cos\phi & \sin\phi \\ -\sin\phi & \cos\phi \end{pmatrix} \begin{pmatrix} e^{i\beta_x'l'} & 0 \\ 0 & e^{i\beta_y'l'} \end{pmatrix} \begin{pmatrix} \cos\phi & -\sin\phi \\ \sin\phi & \cos\phi \end{pmatrix} \begin{pmatrix} 0 \\ E_{0y} \end{pmatrix}, \tag{5}$$

where $\beta_{x,y}'=(2\pi/\lambda)\,n_{\mathit{eff}_{x,y}}$ refer to the propagation constants in the perturbed zone. The explicit expressions for the polarization components $$E_x'' = \sin\phi\cos\phi(e^{i\beta_y'l'} - e^{i\beta_x'l'})E_{0y} \tag{6a}$$

$$E_y'' = (\cos^2\phi\, e^{i\beta_y'l'} + \sin^2\phi\, e^{i\beta_x'l'})E_{0y} \tag{6b}$$

indicate that both polarization components will be excited (and a beating observed) as long as 1) there is a local rotation φ of the polarization axes and 2) the perturbed section is also birefringent. To first order in φ, $$E_x'' \cong \phi(e^{i\beta_y'l'} - e^{i\beta_x'l'})E_{0y} \tag{7a}$$

$$E_y'' \cong e^{i\beta_y'l'}E_{0y} \tag{7b}$$

This result suggests that, as long as the local rotation is small, the initially excited component $E_{0y}$ still dominates and can give rise to a similar coupling at a second coupling point $z_2$ with a minimum of influence from the first coupling point. More generally, a series of N weak coupling points would, in this limit, yield a series of beatings given by:

$$I = I_0 \left[ \frac{1}{2} + \sum_{n=1}^{N} \sqrt{\kappa_n}\, \cos(2\pi B v Z_n) \right], \tag{8}$$

where $\kappa_n$ represents the coupling strength.

To first order in φ, the Fourier spectrum S(Z) of the detected signal is $$S(Z) = \int_{v_{min}}^{v_{max}} e^{i2\pi BZv} \frac{1}{I_o} dv \tag{9}$$

$$S(Z) = \frac{\phi \Delta v}{2} \left[ \exp[i2\pi B(Z-Z_n)\Delta v] \frac{\sin(\pi B(Z-Z_n)\Delta v)}{(\pi B(Z-Z_n)\Delta v)} - \exp[i2\pi B(Z-Z_n-l')\Delta v] \frac{\sin(\pi B(Z-Z_n-l')\Delta v)}{(\pi B(Z-Z_n-l')\Delta v)} \right]. \tag{10}$$

where $\Delta v = v_{max} - v_{min}$.

Close inspection of (10) reveals that a coupling zone of length $l'$ should, in principle, give rise to two peaks, one at $Z_n$ and the other at $\approx Z_n + l'$ (for $B' \approx B$) Whether or not two peaks will indeed be observed depends on the resolution of the sensor.

Using the above-described method to measure the position of the coupling points, the velocity of a coupling point can be determined by measuring the position of the peaks in time and inferring the velocity from it. In this method the velocities are indirectly measured. A direct velocity measurement method is provided hereinafter.

Finally, measurement of the velocity of the coupling points is now discussed. Using single wavelength analysis, real-time monitoring of the separation process can be achieved by determining the velocities $V_n$ of the components. Assuming coupling points moving at different speeds, equation (3) can be written as:

$$I(t) = I_0 \left[ \frac{1}{2} - \sum_{n=1}^{N} \sqrt{\kappa_n} \cos\left(2\pi \frac{B}{\lambda}(Z_{0n} - V_n t)\right) \right], \quad (11)$$

where $Z_{0n}$ represents the initial position of the coupling points. Defining $V' = BV/\lambda$, one can take the Fourier transform of the modulation signal $$S(V') = \int_0^T e^{i2\pi V' t} \left[ \frac{I}{I_o} - \frac{1}{2} \right] dt, \quad (12)$$

where T represents the time length of the recorded signal. A graph of S vs V' will then show discrete peaks corresponding to the different velocities of the coupling points. Each component having its characteristic velocity, a given peak in the spectrum then identifies a specific component. It is thus contemplated that, while coupling points positions are determined by calculating the Fourier integral over the wave number ν, here the Fourier integral is calculated over time t to determine the velocities.

Some alternative embodiments of the invention will now be presented.

A person skilled in the art will appreciate that any of the modified birefringent optical fiber of FIG. 1A, FIG. 1B, FIG. 1C or FIG. 1D could be used in the described distributed optical fiber chemical analysis systems. Alternatively, any other birefringent fiber, as bow-tie fiber, modified to have a channel to circulate a fluid could also be used.

Furthermore, the polarization of light at the input of the optical fiber could alternatively be elliptical or circular but a more complex analysis would then be required.

It should be appreciated that the fluid can be circulated in the channel by providing fluid pressure at the inlet of the channel, fluid vacuum at the outlet, gravity, electrical field or any other force. The fluid could also flow from the light output end of the optical fiber to the light input end.

It should be appreciated that according to the invention, the optical analyzer can either be a spectrum analyzer or an optical detector. In the case of position monitoring, the light source used in a distributed optical fiber chemical analysis system can be any broad optical source or any tunable source. In the case of a broadband source, a suitable spectrum analyzer could be a Fabry-Perot spectrum analyzer, a Michelson interferometer spectrum analyzer or a diffraction grating spectrum analyzer. In the case of a tunable source, the wavelength can be scanned over a predetermined wavelength range while simultaneously measuring the output light using an optical detector. Numerous measurement setups allowing sequential measurements of the spectral response of the interferometer could be suitable.

If velocity alone is to be monitored, the light source can be a single wavelength source and the optical analyzer can be any optical detector.

The embodiments of the invention described above are intended to be exemplary only. The scope of the invention is therefore intended to be limited solely by the scope of the appended claims.

The invention claimed is:

1. An optical waveguide analyzing system, said system comprising:
    a light source system for providing a polarized source light;
    a birefringent optical waveguide optically coupled to said light source system such that said light is to be propagated in said optical waveguide, said optical waveguide having:
        a propagation volume extending along said optical waveguide, with at least a portion of said light to be confined thereto,
        a cladding volume extending along said optical waveguide and surrounding said propagation volume,
        a first and a second polarization axes, and
        a longitudinal channel defined by a channel surface in said cladding volume and adapted to receive a fluid such that said fluid travels along said longitudinal channel, said longitudinal channel being positioned with respect to said propagation volume in such a manner that said fluid traveling in said longitudinal channel is to cause a local variation of the orientation of said polarization axes; and
    an analyzing module optically coupled to said optical waveguide for polarizing an outgoing light and for providing a measurement of an effect of said local variation of orientation on the polarized outgoing light so as to analyze at least one characteristic of said fluid.

2. The optical waveguide analyzing system as claimed in claim 1, wherein said system is a distributed optical waveguide chemical analyzing system for analyzing said fluid and wherein a local channel surface absorption of said fluid causes a local variation of the orientation of said polarization axes.

3. The optical waveguide analyzing system as claimed in claim 1, wherein said fluid has at least a carrier and a component and said analyzing module has a processing unit to calculate, from said measurement, a velocity of said components in said channel.

4. The optical waveguide analyzing system as claimed in claim 2, wherein said light has multiple wavelengths and wherein said measurement has an optical spectrum of said outgoing light as a function of time.

5. The optical waveguide analyzing system as claimed in claim 4, wherein the analyzing module has a processing unit to perform a Fourier transform of said optical spectrum and provide an intensity profile as a function of a position along said optical waveguide, whereby a separation process of said fluid can be characterized.

6. The optical waveguide analyzing system as claimed in claim 5, wherein said fluid comprises a carrier and a component to be analyzed and wherein said processing unit is further to calculate a position of said component in said channel as a function of time.

7. The optical waveguide analyzing system as claimed in claim 1, wherein said light source system comprises a single wavelength source and said analyzing system measures an intensity of said outgoing light as a function of time.

8. The optical waveguide analyzing system as claimed in claim 7, wherein said fluid comprises a carrier and at least two components to be analyzed, the analyzing system having a processing unit to perform a Fourier transform of said intensity and thereby calculate a velocity of said components in said channel, whereby a separation process of said fluid can be characterized.

9. The optical waveguide analyzing system as claimed in claim 1, wherein said optical waveguide is coupled to said light source system such that a polarization of said light is at least mostly aligned with said first polarization axis.

10. The optical waveguide analyzing system as claimed in claim 9, wherein said optical waveguide is coupled to said light source system such that a polarization of said light is slightly misaligned with said first polarization axis.

11. The optical waveguide analyzing system as claimed in claim 1, wherein said propagation volume has a core defined by a core surface, said core surface and said channel surface being positioned with respect to one another such that an evanescent wave of said light is to be propagated at least partly in said channel.

12. The optical waveguide analyzing system as claimed in claim 2, wherein said fluid is mixture and said longitudinal channel has a surface treatment on said channel surface for absorbing components of said fluid.

13. The optical waveguide analyzing system as claimed in claim 12, wherein said surface treatment comprises at least one of a sorbent coating and a porous coating.

14. The optical waveguide analyzing system as claimed in claim 1, wherein said optical waveguide comprises an optical fiber.

15. An optical waveguide wherein a fluid is to travel and wherein light is to be propagated, said optical waveguide comprising:

a propagation volume extending along said optical waveguide, with at least a portion of said light to be confined thereto;

a cladding volume extending along said optical waveguide and surrounding said propagation volume;

a first polarization axis associated with a first effective index and a second polarization axis associated with a second effective index, a value of said first effective index and a value of said second effective index being different in such manner that said optical waveguide is a birefringent waveguide; and a longitudinal channel defined by a channel surface in said cladding volume and wherein said fluid is to travel, said channel being positioned with respect to said propagation volume in such a manner that said fluid traveling in said channel is to cause a local variation of the orientation of said polarization axes.

16. The optical waveguide as claimed in claim 15, wherein said optical waveguide is to be used to analyze said fluid and wherein a local channel surface absorption of said fluid is to cause a local variation of the orientation of said polarization axes.

17. The optical waveguide as claimed in claim 15, wherein said longitudinal channel has a channel center defined on a cross-section of said optical waveguide and said propagation volume has a propagation center defined on said cross-section, said optical waveguide having a first and a second symmetry axes defined on said cross-section and without considering said channel, said channel center and said propagation center defining a line, said line being substantially misaligned with said first and with said second symmetry axes.

18. The optical waveguide as claimed in claim 16, wherein said channel surface has a surface treatment thereon for absorbing components of said fluid.

19. The optical waveguide as claimed in claim 15, wherein said propagation volume has a non-circular core.

20. The optical waveguide as claimed in claim 15, wherein said local variation of the orientation of said polarization axes is due to a local value of a refractive index of said fluid.

* * * * *